United States Patent [19]

Jeffers et al.

[11] Patent Number: 4,488,118

[45] Date of Patent: Dec. 11, 1984

[54] HALOGEN GAS LEAK DETECTOR

[75] Inventors: Edward A. Jeffers; R. Philip McLeroy, both of Hollywood; Jose L. Sacerio, Hialeah, all of Fla.

[73] Assignee: Control Power Systems Inc., Hialeah, Fla.

[21] Appl. No.: 304,483

[22] Filed: Sep. 22, 1981

[51] Int. Cl.$^3$ .............................................. G01N 27/60

[52] U.S. Cl. ...................................... 324/455; 340/632

[58] Field of Search ............... 324/455, 457, 72, 99 D, 324/464; 340/632; 307/296 R, 297; 328/175

[56] References Cited

U.S. PATENT DOCUMENTS 3,742,475 6/1973 Liebermann et al. ............... 340/632

*Primary Examiner*—Michael J. Tokar
*Assistant Examiner*—Kevin D. O'Shea
*Attorney, Agent, or Firm*—Ernest H. Schmidt

[57] ABSTRACT

A method and apparatus for measuring the presence of trace amounts of a halogen gas in ambient air by changes in conductivity of a negative corona in an electrical sensing gap due to the presence therein of such electro-negative gas molecules, utilizes a digital feedback loop sensitive to gap corona current to adjust the high voltage producing the corona discharge to obtain the optimum corona current for best sensitivity irrespective of the concentration of the halogen contaminant present. The presence of the halogen gas contaminant in the air is indicated by a bi-level audible alarm consisting of a periodically interrupted tone the frequency of which goes above or below a base line value to indicate small variations in impurity concentration above or below the base line concentration, and the tone interruption rate of which, at the same time, increases for large impurity concentrations.

3 Claims, 4 Drawing Figures

HALOGEN GAS LEAK DETECTOR

BACKGROUND OF THE INVENTION

This invention relates to electronic instruments for detecting the presence of trace amounts of gaseous impurities in the ambiant atmosphere, it is directed particularly to a portable electronic device for the detection of Freon leaks or the leakage of other gaseous hallides into the surrounding atmosphere in the maintenance and repair of air conditioning and refrigeration systems, for example.

Various types of portable electric instruments utilizing high voltage corona discharge gaps as sensing means in the detection of minute concentrations of foreign gasses in air such as one of the gaseous hallides, have heretofore been devised. Such detectors, which rely on the changes in the sensing gap conductance as being a function of concentration in the ambiant atmosphere of the gaseous impurities to be measured, have found wide application in the detection of refrigerant leaks, such as leakage of Freon in the maintenance and repair of commercial, residential and automotive airconditioning systems. Typically, the magnitude of the voltage applied to a sensing tip comprising the corona discharge gap is manually adjusted until a corona is stricken and a given current flows in the discharge. This current is utilized to energize an audible alarm circuit producing "clicks" or monotonic "beeping" sounds in a loudspeaker at a rate inversely proportional to the current—the greater the current the longer the time interval between "clicks" or "beeps". The component values of the alarm circuit are selected to produce a predetermined "clicking" rate presumed to be readily recognizable when the optimum current flows through the sensing tip corona. In use of such gas detectors, the operator adjusts the high voltage until the right "clicking" or "beeping" rate is obtained. Since the detecting signal of gaseous concentration in the air being measured is an audible "clicking" or "beeping" signal the repetition rate of which increases with increased concentrations of the foreign gas, the signal repetition frequency is not a consistent indicator of a given concentration. Thus, because of perceptual variations, what seems like a optimum "clicking" or "beeping" rate to one operator ordinarily does not to another operator, optimum sensing tip current flow adjustment is rarely achieved, with consequent decrease in instrument sensitivity. Additionally, the operator is distracted because of the nearly continuous need to adjust the high voltage being applied to the sensing tip discharge gap in an attempt to maintain optimum current flow or sensitivity adjustment in the face of a changing gaseous mixture environment. These deficiencies necessitate inordinate attention to the sensing readjustment of the instrument, especially in the detection of small leakage rates of 0.1 oz. per year, for example.

SUMMARY OF THE INVENTION

It is, accordingly, the principal object of this invention to provide a novel and improved electronic leak detector which obviates the deficiencies of electronic halogen gas leak detectors heretofore known.

A more particular object of the invention is to provide a halogen leak detector of the type described wherein the sensing tip and its associated control and detecting circuitry incorporates a digitally controlled sensing tip current feedback loop nulling means for automatically setting the system to the optimum one of a great number of programmed operating points, also referred to hereinbelow as a base line setting, of the sensing tip to best match the particular atmosphere being searched for halogen gas leakage or content. Thus, if the leak detector is turned on in a clean atmosphere and then moved into an atmosphere containing 100 ppm halogen gas, the alarm will signal the presence of the gas by the "beep" tone increasing in beep repetition rate or frequency. In momentarily activating the reset switch, the instrument will program "out" the 100 ppm halogen gas by automatically selecting a new operating point or base line setting better suited to match the environment and pinpoint the leak.

Another object is to provide a halogen gas leak detector of the character described wherein the audible "beeping " signal, in addition to signaling increased concentrations of a halogen gas in the surrounding atmosphere by increase in repetition frequency above a base line setting, also incorporates means for continuously increasing the pitch or tone of the individual beeps the "beeping" alarm signal, variations of the tone signal being particularly sensitive to minor variations in the contaminated atmosphere being measured, thereby alerting the operator as to whether he is moving closer to, (higher pitch tone), or farther away from, (lower pitch tone), the leak source. This change in tone sensitivity is referred to as bi-level sensitivity.

Another object of the invention is to provide a halogen gas leak detector of the character described wherein the high voltage sensing tip and its associated control and detecting circuitry are of such design as results in a very stable, reproducable, audible alarm halogen gas sensing device of enough sensing range as to be able to generate discernible signals from contaminations produced by Freon leakage rates of 0.1 oz. per year to such massive contaminations as those produced by an open container of liquid Freon.

Other objects, features and advantages of the invention will be apparent from the following description when read with reference to the accompanying drawings. In the drawings, wherein like reference numerals denote corresponding parts throughout the several views.

Figure 1:
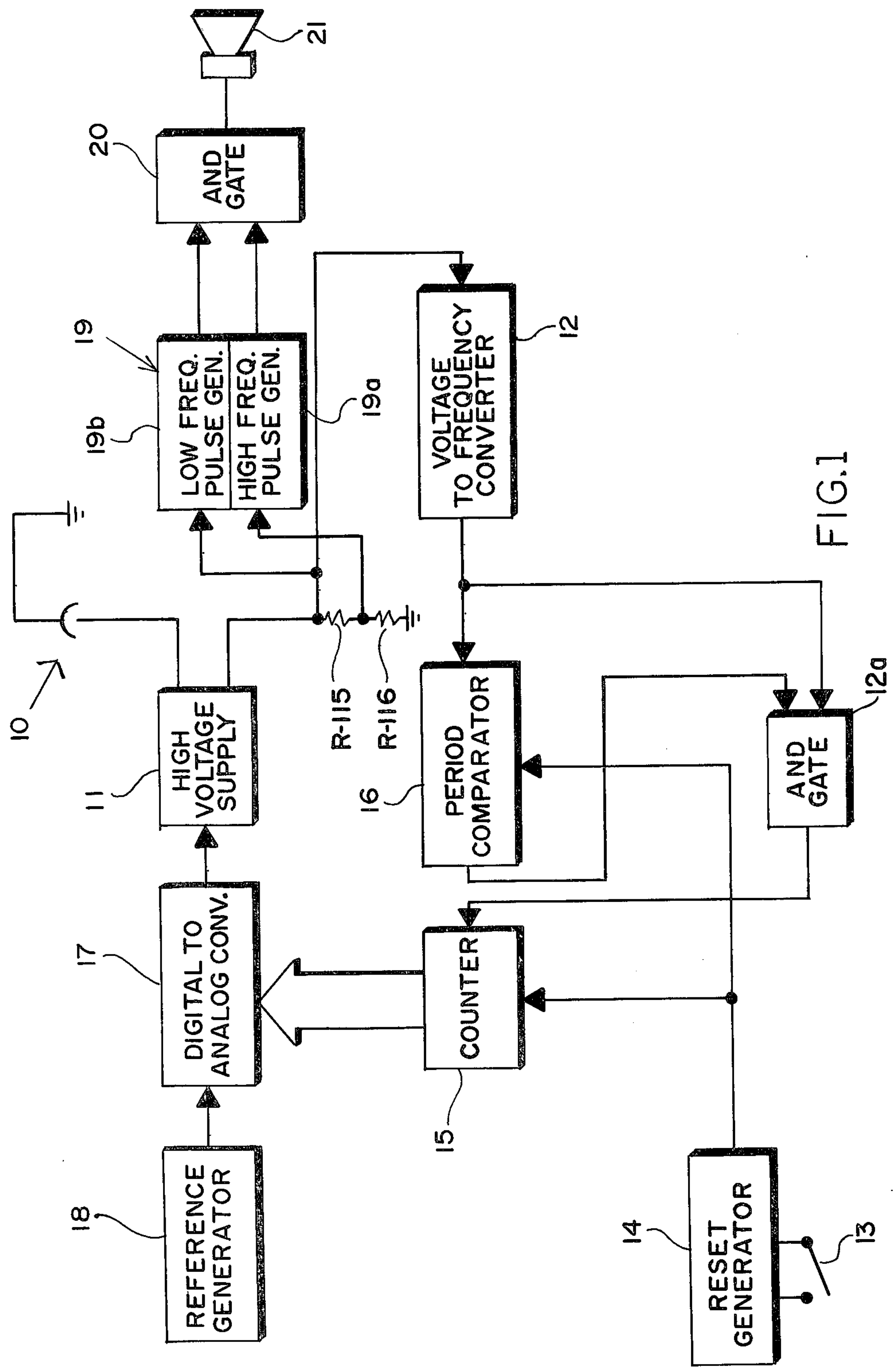
FIG. 1 is a block diagram of a typical halogen leak detector embodying the invention.

The method of detection consists of the generation in the atmosphere to be monitored of a D.C. negative corona discharge between a pair of electrodes immersed in said atmosphere. The electrodes consist of an internal hemispherical shell surface and the point of a very sharp straight electrode member spaced outwardly of the center of said hemispherical shell along the axis thereof. The electrode assembly, referred to herein as the sensing tip, is identified generally by reference numeral 10 in FIGS. 3 and 4, and described in detail hereinbelow. A D.C. potential is applied across the sensing tip electrodes, of sufficient amplitude as to produce a corona between them in the absence of halogen gas. The current flow through the corona is used as the variable parameter to indicate the presence of halogen gas; the amplitude of this current becoming smaller as the concentration of halogen gas in the atmosphere where the corona is set up increases.

Referring first to the block diagram of FIG. 1, illustrating a preferred embodiment of the invention, the high voltage supply 11 in series with the sensing tip 10 for supplying corona current thereto is indirectly controlled by the period of a voltage-to-frequency converter 12 for establishing the correct operating current in the sensing tip. Whenever the system is turned on, as by switch 13, reset generator 14 clears counter 15 and the period comparator 16. Under these conditions, a minimum or starting voltage is developed at the output of the high voltage supply 11 and applied to the sensing tip 10. The current flowing in the resulting corona discharge of the sensing tip flows through voltage divider resistors $R_{115}$ and $R_{116}$ developing a proportionate feedback voltage which is applied to the input of the voltage-to-frequency converter 12. The voltage-to-frequency converter 12 produces a train of impulses at its output which are inversely proportional to the magnitude of the voltage drop across series resistors $R_{115}$ and $R_{116}$ and thus, when the system is turned on, the voltage-to-frequency converter 12 produces output pulses at a high rate, since the current through the sensing tip 10 will be at a minimum.

The pulses from the voltage-to-frequency converter 12 are analyzed by the period comparator 16 to determine if the period or time interval between pulses has reached a pre-set maximum or threshold value. To this end AND gate 12*a* communicates the variable frequency pulse train output from voltage-to-frequency converter 12 to counter 15 under control of period comparator 16. In other words, AND gate 12*a* allows pulses pulses to be counted by counter 15 as long as the period of the pulses in the pulse train is below a threshold or maximum value level determined by period comparator 16. If the period of the pulses is below the preset level determined by period comparator 16, they are allowed to pass to the counter 15, where they are accumulated. Above that threshold, period comparator 16 closes AND gate 12*a*, stopping the counting process in counter 15.

The output of the counter 15, which increases monotonically with time as the pulses are accumulated, is utilized to drive a digital to analog converter 17. The function of the digital to analog converter 17 is to act as a digitally controlled potentiometer applying an increasing fraction of the output of the reference generator 18 to the input of the high voltage supply 11, where it is converted to a monotonically increasing high voltage output.

As the high voltage to the sensing tip 10 increases, the corona current also increases, causing a corresponding lengthening of the period of the pulses at the output of the voltage-to-frequency converter 12. Eventually, the time interval between pulses reaches the preset value at the period comparator 16 which changes state and prevents any more pulses from accumulating in the counter 15. Since the count is what determines the output of the high voltage supply 11, no further changes can occur in the high voltage applied to the sensing tip 10 after the period comparator 16 has changed states and, at this time, the balancing operation is completed with the optimum operating current flowing through sensing tip 10.

Since the time interval to which the period comparator 16 is referred is always constant, it will be apparant that no ambiguities due to operator judgment can occur, and the tip is always set to the same optimum operating point at the end of the balancing cycle.

After the sensing tip 10 is balanced, the high voltage applied to it remains constant, allowing the concentration of halogen gas in the atmosphere surrounding the tip to change the current of the corona discharge.

Changes in the corona current are translated into corresponding voltage changes across resistors $R_{115}$ and $R_{116}$, and $R_{116}$ alone. These two signals are applied to the inputs of two voltage controlled pulse generators in the dual alarm 19. The smaller of the two signals (the voltage drop across $R_{116}$) is used to modulate the frequency of the pulse generator in the alarm 19*a* which operates at the higher baseline frequency. The larger signal (the voltage drop across $R_{115}$ and $R_{116}$) modulates the frequency of the pulse generator in the alarm 19*b* which operates at the lower baseline frequency. The AND gate 20 combines the outputs of the two pulse generators and drives the loudspeaker 21 to produce an audible alarm which informs the operator about the presence of halogen gases in the vicinity of the sensing tip 10. In the preferred embodiment of the invention, the high frequency pulse generator 19*a* is driven by the voltage drop across voltage divider resistor $R_{116}$ proportionate to current flowing in the sensing tip 10, to modulate the low frequency pulse generator 19*b*. The frequency of the low frequency pulse generator 19*b* is controlled by the comparatively large current dependent voltage drop across series connected voltage divider resistors $R_{115}$ and $R_{116}$. With this circuitry, operation is such that an increase in halogen gas concentration relative to the atmosphere in which the tip is balanced, results in an audio signal which not only increases in the rate at which the high frequency audio tone or "beep" is interrupted but also increases in the frequency or pitch of the audio tone. Conversely, a decrease in halogen gas concentration relative to the atmosphere in which the tip is balanced produces a reduction both in the rate at which the high frequency audio tone or "beep" is interrupted and the frequency or pitch of the audio tone.

Rebalancing of the sensing tip to optimum corona current for the atmosphere to be detected for halogen gas contamination is accomplished by the operator simply by pressing push button switch 13 activating reset generator 14 to clear the counter 15 and the period comparator 16. This operation restarts the above described balancing cycle, at the end of which the sensing tip 10 is again operating under optimum conditions for the atmosphere being examined for halogen gas content at that time. Movement of the sensing tip away from the contamination thereafter produces a decrease in signal interruption rate below that of the new or rebalanced base line setting.

DETAILED DESCRIPTION OF THE ELECTRICAL CIRCUITRY

Figures 2, 3, 4:
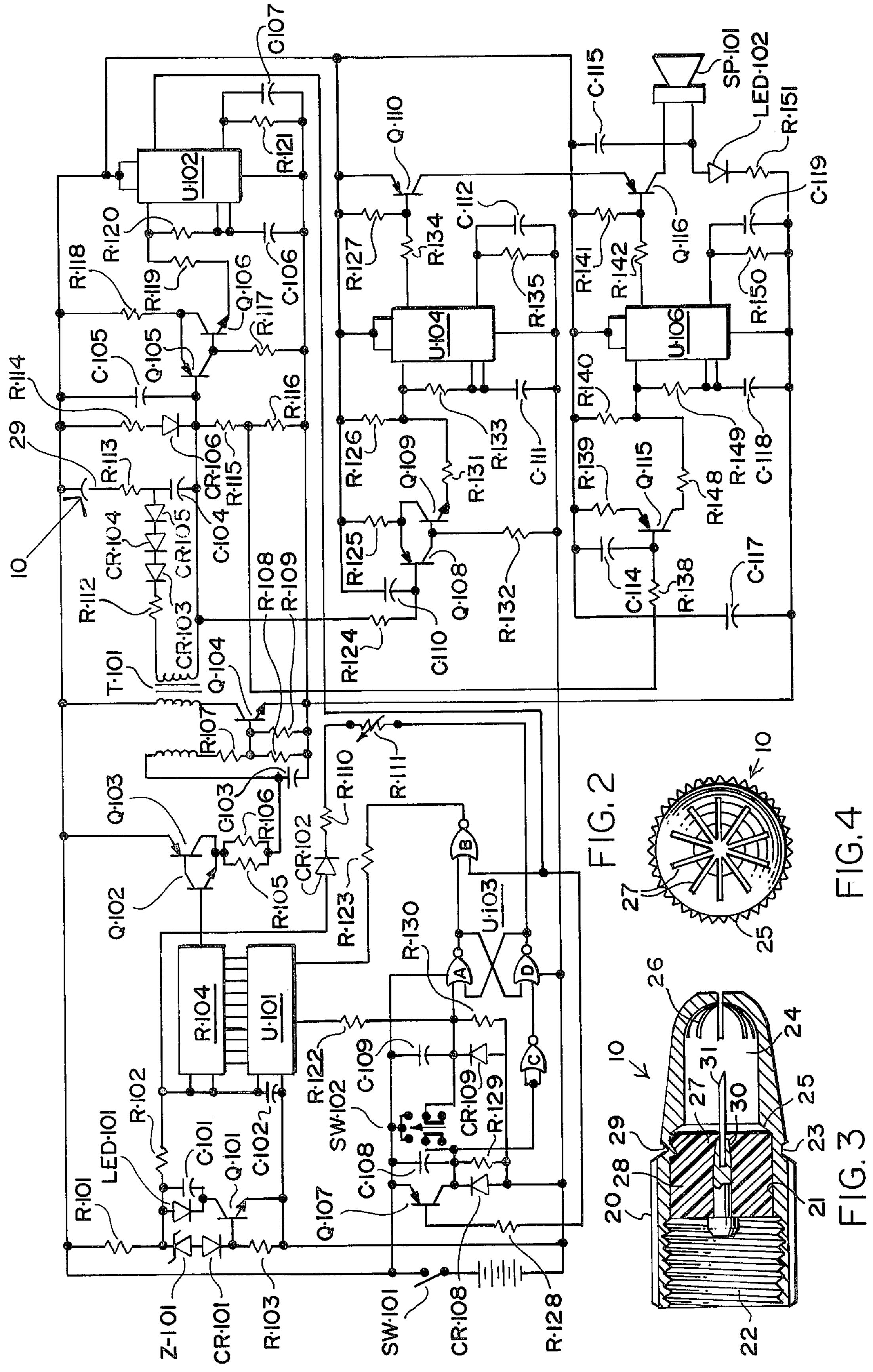
FIG. 2 is an electrical schematic drawing thereof.
Fig. 3 is a side view, on an enlarged scale and partially in longitudinally cross-section, of the sensing tip.
FIG. 4 is a front end view of the sensing tip illustrated in FIG. 3.

Referring now in detail to FIG. 2 of the drawings, the high voltage D.C. generator supplying operating voltage to the sensing tip 10 comprises blocking oscillator transformer T-101, series connected half-wave diodes CR-103, CR-104, CR-105, filter resistor R-112 and condenser C-104, the output of which generator is fed through current-limiting resistor R-113 to the anode 29 of said sensing tip. FIGS. 3 and 4 illustrate in detail the sensing tip 10 symbolically illustrated in the block and schematic diagrams of FIGS. 1 and 2, respectively.

As illustrated in FIGS. 3 and 4, in its preferred form the tip 10 comprises a cylindrical, electrically-conductive shell member 20, which may be machined of aluminum, for example, and which is formed with a first concentric bore 21, the outer portion of which is internally threaded, as at 22, for screw-thread connection with the distal end of a flexible electrical conductor conduit (not illustrated) extending from the instrument housing. The outer periphery of the shell member 20 is formed with an annular groove 23 in registry with an inner end portion of the internal bore 21 thereof, for the purpose hereinafter appearing. The inner end of the first concentric bore 21 merges with a second, reduced-diameter bore 24, defining therewith an annular shoulder 25. The inner end of the second concentric bore 24 terminates in hemispherical end wall 26. The tip or distal end of the conductive shell member 20 is rounded at the outside to define a wall thickness of approximately one-third the length of the radius of generation of the hemispherical end wall surface 26. To provide for the entrance of the gaseous atmosphere to be sensed, the outer end of the shell member 20 is axially slotted, as by plurality of equidistantly-spaced slots 27. The slots 27 will preferably extend just short of a transverse plane including the origin of the radius of generation of the inner hemispherical end wall surface 26.

Fitted within the first concentric bore 21 of the tip shell member 20 is a cylindrical tip shell insulator 28, which may be fabricated of a tough, synthetic plastic material of high dielectric strength. The insulator 28 is fixed in place by swaging the shell member 20 at one or more points within groove 23 by use of a blunt punch, as indicated at 29.

Friction fitted within the central, small-diameter bore in the insulator 28 is a headed metal conductor pin 30 the tip of which has attached thereto, such as by swaging in an axial bore, the pointed electrode 31. The pointed electrode 31 will preferably be of a fine gauge wire, copper wire for example, the end of which is pointed such as by having been cut at an angle. As best illustrated in FIG. 3, the lengths of the second concentric bore 21 and the pointed electrode 31 are such that the slots 27 extend axially only to about one-half the distance to the end of said pointed electrode within the ionization chamber defined by said second concentric bore and the hemispherical end wall surface 26.

The above described physical characteristics of the sensing tip 10 have been found experimentally to provide optimum sensitivity in halogen gas detection when used as the D.C. corona discharge gap in combination with the associated electronic energizing and sensing circuitry herein disclosed.

The current through the corona discharge in tip 10 is made to flow through the voltage divider comprising resistor R-114, diode CR-106, and resistors R-115 and R-116. This voltage divider establishes the no-signal operating point for the system and also provides a load to convert current changes in the corona discharge into voltage changes.

The voltage-to-frequency converter made up of integrated circuit U-102, resistors R-119, R-120 and R-121, and condensers C-106 and C-107 and driven by a current source comprising cascade connected transistors Q-105, Q-106, is used to sense the voltage level at the junction of diode CR-106 and resistor R-115 and convert it to a pulse train having a period proportional to the voltage level.

The pulses from pin 3 of integrated circuit U-102 are sent to binary counter U-101 by way of "NOR" gate "B" of U-103. This gate is enabled by the "A" side of the "flip-flop" made up of gates "A" and "D" of U-103. The pulses at pin 3 of U-102 also go to the base of transistor Q-107 which discharges condenser C-108 at the arrival of each pulse, keeping the input of inverter "C", in U-103, at a logic "1" level.

On turn-on of switch 101, a voltage pulse through condenser C-109 resets the "flip-flop" enabling gate "B" in U-103 and allowing pulses to pass to counter U-101. At the same time, transistor Q-107 maintains condenser C-108 discharged. If the period of the pulses becomes long enough, condenser C-108 will have time to charge through resistor R-129, changing the state of the output of inverter "C" and setting the "flip-flop". Setting the "flip-flop" disables gate "B" and no more pulses are allowed to pass to counter U-101.

The output of counter U-101 is a 10 bit long binary number which controls a binary attenuator or ladder network, R-104. This resistor network is designed to function as a voltage divider producing an output signal which is a fraction of the voltage applied to its input. This fractional voltage is directly proportioned to the binary output of the counter and, in this manner, as the binary output from counter U-101 increases, a large portion of the input voltage to resistor R-104 is present at the input of buffer amplifier comprising transistors Q-102, Q-103. This amplifier drives the blocking oscillator through resistors R-105 through R-109. It can be seen, then, that the output of counter U-101 controls the amount of high voltage in a digital manner.

The nulling cycle is initiated by turning the system on with switch SW-101 or actuating reset switch 13. At this point, the output pulses from counter U-102 are allowed to advance counter U-101 from the zero state to the point where enough high voltage is present to cause the period of the pulse train to have a preset value set by the time constant of condenser C-108 and resistor R-129 and the threshold of gate "C" in counter U-103. When this period is reached, the counter is stopped by setting the "flip-flop" (gates "A" and "D" of U-103) and inhibiting the pulse input to the counter.

After the nulling cycle has been completed, the high voltage present at the electrode pair of the sensing tip 10 is kept constant by the regulation of the reference generator comprising transistor Q-101, zenor Z-101 and associated components. The presence of halogenated gases in the atmosphere of the discharge is thus allowed to change the corona current, proportionately, which, in turn controls the change in pitch feature of the bi-level alarm indicating small variations of impurity concentration above and below the base line concentration. These changes are used to drive a pair of voltage-to-frequency converters (hereinafter described) which provide the "bi-level" audible alarm.

Resistors R-102, R-110, R-111 and diode CR-102 form an adjustable voltage divider which comes into play after the nulling cycle, when the output of gate "D" of counter U-103 goes low. Resistor R-111 is set so as to slightly decrease the high voltage to the electrode pair and compensate for any *overshoot* in the digital loop which may result in too much discharge current and consequently, in an elevated threshold and decreased sensitivity.

One of the voltage-to-frequency converters normally operates at a higher base frequency than the other. This generator (referred to as high-frequency pulse generator 19a in FIG. 1) is composed of a current source comprising cascade connected transistors Q-108, Q-109, resistors R-124, R-125, capacitor C-110, current-controlled, astable multivibrator U-104, resistors R-126, R-131, R-133 and R-135, condensers C-111, C-112 and driver circuitry comprising resistors R-134 and R-127, and transistor Q-110. It provides information about small changes in halogen gas concentration—both increase and decrease—around the null concentration.

The other voltage-to-frequency converter (referred to as low-frequency pulse generator 19b in FIG. 1) operates at a much lower base frequency and has a predetermined threshold. This generator is composed of a current source comprising transistor Q-115, resistors R-138 and R-139, capacitor C-114, current-controlled, astable multivibrator U-106, resistors R-148, R-140, R-149, R-150, capacitors C-118, C-119, and driver circuiting comprising resistors R-141, R-142 and transistor Q-116. Operating at a predetermined threshold, it indicates the presence of larger concentration of halogen gases.

Drivers comprising transistors Q-110 and Q-116 are connected in totem-pole fashion with the collector of Q-116 driving the speaker SP-101 and visual alarm LED-102 through resistor R-151. This arrangement allows two sounds to be heard at the speaker: one high pitch tone which indicates small variations in impurity concentration with periodic interruptions which increase in frequency as larger concentrations of halogen gases are detected. As referred to above, this audible signal is termed a "bi-level" alarm since it carries information about two ranges of halogen gas concentration.

As an aid to those skilled in the art and having the right to practice the invention, the following listed values and identifications of the circuit components which have been found to best fulfill the objectives of the invention are given by way of example:

| RESISTORS | | | |
|---|---|---|---|
| R-101 | 220 ohm | R-125 | 470 ohm |
| R-102 | 470 ohm | R-126 | 10 Megohm |
| R-103 | 1000 ohm | R-127 | 470 ohm |
| R-104 | Ladder Network | R-128 | 1 Kilohm |
| R-105 | 2.7 Kilohm | R-129 | 470 Kilohm |
| R-106 | Selected to obtain 3000 Volts DC maximum from High Voltage Supply | R-130 | 510 Kilohm |
| | | R-131 | 2.2 Kilohm |
| R-107 | 560 ohm | R-132 | 510 Kilohm |
| R-108 | 2.2 Kilohm | R-133 | 150 Kilohm |
| R-109 | Selected to obtain 1000 Volts DC minimum from High Voltage Supply | R-134 | 470 ohm |
| | | R-135 | 10 Kilohm |
| R-110 | Coarse padding to compensate for loop overshoot | R-138 | 100 Kilohm |
| | | R-139 | 39 Kilohm |
| R-111 | Fine padding to compensate for loop overshoot | R-140 | 2.2 Megohm |
| R-112 | 1 Megohm | R-141 | 470 ohm |
| R-113 | 1 Megohm | R-142 | 470 ohm |
| R-114 | 100 Kilohm | R-148 | 2.2 Kilohm |
| R-115 | 62 Kilohm | R-149 | 20 Kilohm |
| R-116 | 510 Kilohm | R-150 | 10 Kilohm |
| R-117 | 1 Megohm | R-151 | 10 ohm |
| R-118 | 6.8 Kilohm | | |
| R-119 | 2.2 Kilohm | | |
| R-120 | 20 Kilohm | | |
| R-121 | 10 Kilohm | | |
| R-122 | 33 Kilohm | | |
| R-123 | 33 Kilohm | | |
| R-124 | 100 Kilohm | | |

-continued

| CAPACITORS | TRANSISTORS |
|---|---|
| C-101 .01 mfd | Q-101 2N2222 |
| C-102 1 mfd | Q-102 2N2222 |
| C-104 .0047 mfd | Q-103 2N2907 |
| C-105 .1 mfd | Q-104 MPS UOIA |
| C-106 .01 mfd | Q-105 2N2907 |
| C-107 4.7 mfd | Q-106 2N2222 |
| C-108 1 mfd | Q-107 2N2907 |
| C-109 1 mfd | Q-108 2N2907 |
| C-110 1 mfd | Q-109 2N2222 |
| C-111 .22 mfd | Q-110 2N2907 |
| C-112 4.7 mfd | Q-115 2N2907 |
| C-114 1 mfd | Q-116 2N2907 |
| C-115 47 mfd | |
| C-117 47 mfd | |
| C-118 .01 mfd | |
| C-119 4.7 mfd | |

| DIODES | INTEGRATED CIRCUITS |
|---|---|
| CR-101 IN914 | U-101 MC14040 |
| CR-102 IN914 | U-102 555 |
| CR-103 IN4007 | U-103 MC 4001 |
| CR-104 IN4007 | U-104 555 |
| CR-105 IN4007 | U-106 555 |
| CR-106 IN914 | |
| CR-108 IN914 | |
| CR-109 IN914 | |
| Z-101 LM336 | |

While we have illustrated and described herein a preferred embodiment of our halogen gas leak detector, this embodiment is presented by way of example only and not in a limiting sense. The invention, in brief comprises all the embodiments and modification coming within the scope and spirit of the following claims.

What we claim as new and desire to secure by Letters Patent is:

1. Apparatus for measuring the presence of trace amounts of a halogen gas contaminant in ambient air comprising, in combination, a sensing tip having a pair of electrodes defining an air gap, a high-voltage generator, said high-voltage generator having a high-voltage output circuit supplying a potential to said pair of electrodes for establishing a negative corona discharge current across said air gap in the continuous corona range, means for producing a digital signal, means including a digital signal feedback loop controlled by said sensing tip corona discharge current for adjusting said high-voltage potential to obtain optimum sensing tip corona discharge current for high sensitivity to halogen impurity concentration irrespective of the contaminant concentration present, and electrical indicator means controlled by the corona current in said sensing tip.

2. Apparatus as defined in claim 1 wherein said electrical indicator means comprises an audible alarm, said audible alarm comprising a periodically interrupted audible tone or "beep" the frequency of which goes above or below a base-line value to indicate variations in the purity concentration above or below a base-line concentration by proportional changes in pitch.

3. In apparatus for detecting trace amounts of halogen gas in the air, a sensing device, a dual level audible alarm circuit controlled by said sensing device, said dual level audible alarm circuit being operative to produce periodically interrupted "beep" tone signals the interruption repetition rate of which increases with increased concentration of halogen gas in air detected above a preset level, and the pitch of which tone signals varies up and down, respectively, with variations in concentration of halogen gas in air detected above and below said preset level.

* * * * *